United States Patent [19]

Shmakov et al.

[11] 4,027,233
[45] May 31, 1977

[54] CONTACTLESS INDUCTANCE PICKUP FOR DETECTING THE INTERFACE OF TWO MEDIA

[76] Inventors: Eduard Ivanovich Shmakov, ulitsa Engelsa, 19, kv. 18; Boris Izrailevich Medovar, ulitsa A. Barbjusa, 22/26, kv. 109; Anatoly Ivanovich Chvertko, bulvar Lesi Ukrainki, 2, kv. 739; Vladimir Vasilievich Koval, ulitsa P. Tychiny, 1, kv. 298; Vyacheslav Georgievich Fedotenkov, ulitsa Kreschatik, 29, kv. 45; Oleg Petrovich Bondarenko, ulitsa Kreschatik, 15, kv. 34; Anatoly Iosifovich Kravchuk, ulitsa Semashko, 10, kv. 54; Alexandr Mikhailovich Marchenko, ulitsa Stroitelei, 17, kv. 18; Alexei Georgievich Bogachenko, ulitsa Miljutenko, 15/2, kv. 141, all of Kiev, U.S.S.R.

[22] Filed: June 9, 1975

[21] Appl. No.: 584,928

Related U.S. Application Data

[63] Continuation of Ser. No. 490,993, July 23, 1974, abandoned.

[30] Foreign Application Priority Data

July 23, 1973  U.S.S.R. .......................... 1947940

[52] U.S. Cl. ......................... 324/34 R; 73/DIG. 1; 164/4; 164/154; 318/642; 340/244 R
[51] Int. Cl.² ...................................... G01R 33/12
[58] Field of Search .......... 324/34 R, 40; 340/244, 340/246, 195, 196, 199; 73/290 R, DIG. 5; 318/642, 652, 653, 656; 164/4, 154, 155

[56] References Cited

UNITED STATES PATENTS

| | | | |
|---|---|---|---|
| 3,366,873 | 1/1968 | Miller et al. | 324/40 |
| 3,511,580 | 5/1970 | Eckhardt et al. | 324/40 |
| 3,519,060 | 7/1970 | Vischolis | 164/155 |
| 3,670,801 | 6/1972 | Crowell et al. | 165/154 |

FOREIGN PATENTS OR APPLICATIONS

| | | | |
|---|---|---|---|
| 834,783 | 5/1960 | United Kingdom | 164/4 |
| 153,787 | 7/1963 | U.S.S.R. | 324/40 |

OTHER PUBLICATIONS

Kravchuk et al., Extreme Metal Bath Level Regulator, Automaticheskay Suarka (U.S.S.R.), No. 8 (221), 1971, pp. 56–57.

Primary Examiner—Robert J. Corcoran

[57] ABSTRACT

A contactless inductance interface pickup, having within an external housing an auxiliary housing installed, and formed as a pot, with at least the bottom thereof being constructed from a non-magnetic material, and a clearance between the external housing and the auxiliary housing wherethrough a cooling agent flows around the pickup. Inside the auxiliary housing, in immediate proximity to the bottom thereof, a magnetic circuit is disposed with at least one measuring winding and at least one energized winding.

12 Claims, 7 Drawing Figures

CONTACTLESS INDUCTANCE PICKUP FOR DETECTING THE INTERFACE OF TWO MEDIA

This is a continuation of application Ser. No. 490,993 filed July 23, 1974, now abandoned.

BACKGROUND OF THE INVENTION

The present invention relates to interface pickups and, more particularly, to a contactless inductance interface pickup designed especially for use in electric-metal-lurgical installations for smelting metals and metal alloys, as well as in electroslag welding facilities.

The interface of two media differing in specific density and resistivity of which at least one is electrically conductive and non-magnetic, maybe determined with the use of contactless and contact pickups.

The contact interface pickups are formed as a horizontal cooled probe and a vertical cooled probe. The horizontal cooled probe is disposed in the forming wall, a crystallizer or a welding shoe, and is electrically insulated from the wall. With the probe so disposed, the slag-metal interface may be determined. The vertical cooled probe is disposed in the forming wall above the fluid slag to determine the air-fluid slag interface. Voltage from an independent source is impressed on the probes and on the ingot being cast or on the workpiece being welded. As soon as the current through the probe-metal or the probe-fluid slag circuit reaches the metal bath or the fluid slag, its magnitude sharply increases, indicating the interface of the two media.

These pickups, however, have a major disadvantage in that the operation of the pickups depends by and large on the rate of coolant consumption. As the coolant consumption increases, slag particles adhere to the probe end and solid dify, forming an obstruction to the passage of electric current. As the coolant consumption decreases, the probe melts which gives rise to an emergency situation, for liquid finds ingress into the fluid slag or the metal bath. Another serious disadvantage of contact pickups prohibitive to their large-scale application is that layers of molten metal are formed between the horizontal probe and the metal bath which, upon solidification, short out the probe-metal circuit.

One prior art contactless inductance interface pickup is an attachable contactless inductance pickup which comprises two energized windings disposed on the extreme poles of a magnetic circuit and a measuring winding disposed on the central pole. Between one of the extreme poles of the magnetic circuit and its central pole, a vessel is disposed containing two media whose interface is to be determined.

The attachable pickup determines the air-molten metal interface when placed at the wall of a pot or ladle. However, it cannot be employed in the processes of electroslag, plasma-arc and electron-beam remelting or in electroslag welding, for such a pickup can only operate when the vessel containing the two media whose interface to be determined is constructed from a non-magnetic material.

It is likewise known to employ a contactless interface pickup for determining the interface of two media differing in specific density and resistivity of which at least one is electrically conductive and non-magnetic. This pickup has a cooled housing with a cover which houses an open magnetic circuit with at least one measuring winding and an energized winding, the poles of the magnetic circuit being oriented toward the interface to be determined.

The magnetic circuit of the pickup is trident-shaped, and its energized and measuring windings are poled in opposition. Since the magnetic circuit with its windings must be disposed in immediate proximity to the interface, the housing within which the magnetic circuit is disposed is to be cooled with a cooling agent. In order to protect the windings and the magnetic circuit against the cooling agent, they are embedded in a cold-curing epoxy resin. However, the embedding procedure fails to pressurize the sites where the leads of the windings extend through the resin and out of the housing.

Another disadvantage of this latter known pickup is the difficulty in controlling the clearance between the magnetic circuit poles and the bottom of the housing, i.e. the interface of the two media, which is required due to the imbalance of the zero signal. This difficulty stems from the fact that the magnetic circuit cannot be moved inside the housing in the course of operation without cutting off the coolant supply; and should the coolant supply be interrupted even for a short time, the pickup housing comes into direct contact with molten metal, which renders the pickup inoperative.

There is still a further disadvantage, viz. cracking of the resin in which the magnetic circuit is embedded due to the sharp fluctuations of the heat load, with the result that the coolant finds ingress to the windings, shorting them out.

SUMMARY OF THE INVENTION

It is an object of the present invention to provide a highly reliable contactless inductance interface pickup.

Accordingly, a contactless inductance interface pickup is provided for detecting the interface of two media differing in specific density and resistivity of which at least one is electrically conductive and non-magnetic, comprising a cooled external housing with a cover which houses an open magnetic circuit with at least one measuring winding and an energized winding with the poles being oriented toward the interface, which, in accordance with the invention, is provided with an auxiliary housing formed as a pot whereof at least the bottom is constructed from a nonmagnetic material, the pot being rigidly secured inside the external housing so that a clearance is defined therebetween to allow passage of a coolant flow, and the magnetic circuit with the windings being disposed within the auxiliary housing immediately proximate to the bottom thereof, the thickness of the bottom being such as to allow the magnetic field of the pickup to reach the interface.

It is preferred that the magnetic circuit be so disposed within the auxiliary housing that the poles thereof are in contact with the bottom of the auxiliary housing.

It is recommended that the magnetic circuit be provided with a mechanism for displacing the magnetic circuit relative to the bottom of the auxiliary housing.

The mechanism should desirably comprise a non-magnetic spring-loaded plate fixed on the magnetic circuit and three rods, one end of each rod being movably secured in the cover of the external housing, whereas the other end of each rod is formed as a spherical bearing being received in a respective aperture formed in the plate, one of the apertures being disposed on the longitudinal axis of the auxiliary housing, whereas the other two apertures are so disposed as to lie in two planes, one parallel and one perpendicular to the plane of the magnetic circuit, and passing through each of the latter two apertures and the aperture disposed on the longitudinal axis of the auxiliary housing.

The bottom of the external housing and the bottom of the auxiliary housing are advantageously spherical shaped, the radius-vectors of curvature thereof being oriented in the same direction.

It is further preferred that the thickness of the auxiliary housing bottom be within 0.05 to 0.35 mm.

The non-magnetic material from which the auxiliary housing bottom is constructed is advantageously an austenitic steel or a titanium alloy whose resistivity is greater than $50.10^{-6}$ ohms.cm.

The above-described design of the proposed contactless inductance interface pickup provides greater durability and ease of maintenance, for the magnetic circuit together with the windings can be replaced while the pickup is in service.

BRIEF DESCRIPTION OF THE DRAWING

The invention will be further understood by reference to the following description of specific embodiments thereof taken in conjunction with the accompanying drawings, wherein.

DETAILED DESCRIPTION OF THE PREFERRED EMBODIMENT

Figure 1:
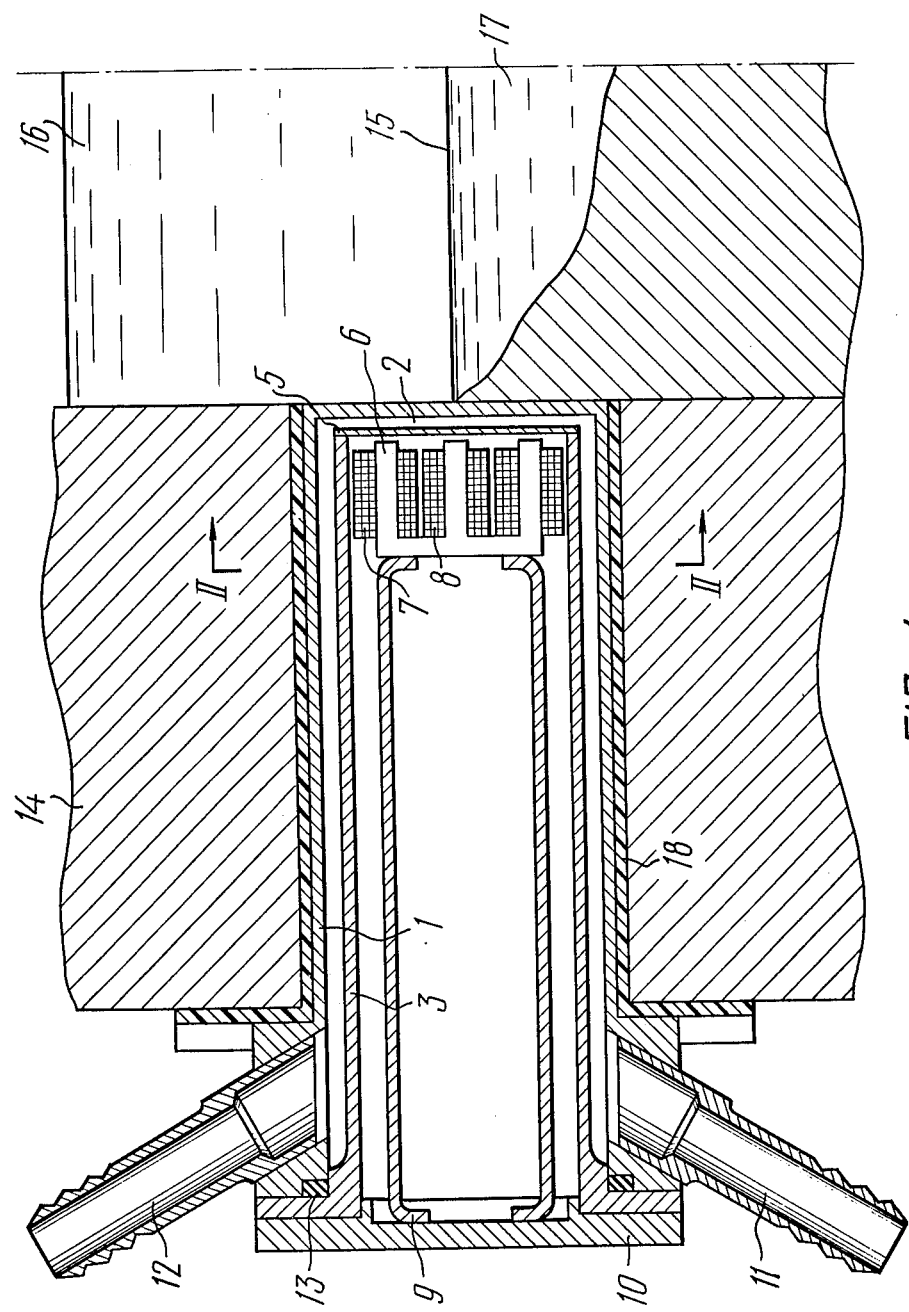
FIG. 1 is a schematic representation of portion of an electroslag remelting facility housing the proposed interface pickup (longitudinal section)
Figure 2:
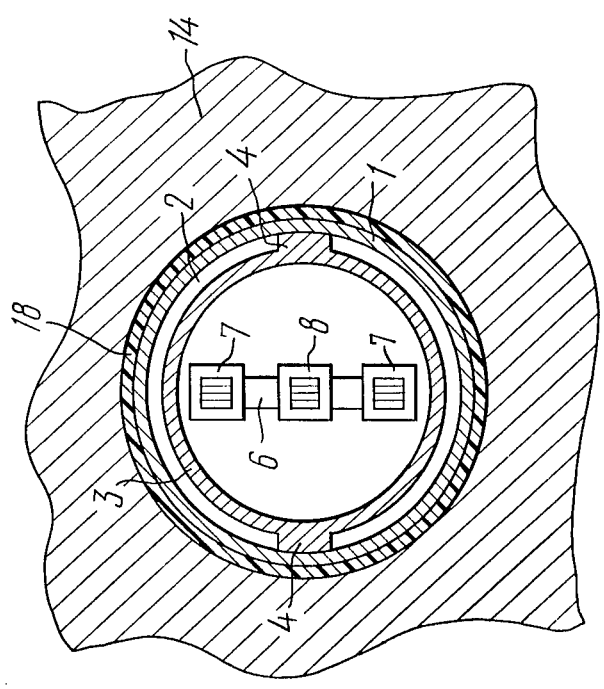
FIG. 2 is a diagrammatic view of a section taken along the line II—II of FIG. 1.

Referring now to the drawings, there is shown a contactless inductance interface pickup for detecting the interface of two media differing in specific density and resistivity of which one is electrically conductive and non-magnetic, which comprises a housing 1 (FIG. 1) formed as a cylindrical pot constructed from a non-magnetic material, which in this case is an austenitic steel having a resistivity of $50.10^{-6}$ ohms.cm. The housing 1 accomodates a rigidly secured auxiliary housing 3 likewise formed as metal pot with two longitudinal projections 4 (FIG. 2) formed on the outer surface thereof, the auxiliary housing so installed inside the housing 1 as to define therewith a clearance 2 allowing a coolant to flow around the pickup, and the two longitudinal projections 4 define two passages with the clearance 2 of the auxiliary housing 3 installed inside the housing 1. The thickness of bottom 5 (FIG. 1) of the auxiliary housing 3 is such that the magnetic field of the pickup can reach the interface of the two media. In the embodiment being described, the bottom 5 is 0.1 mm thick, and the bottom 5 as well as the lateral surface of the housing 3 are constructed from an austenitic steel having a resistivity of $50.10^{-6}$ ohms.cm.

Inside the auxiliary housing 3, in immediate proximity to the bottom 5, an open trident-shaped magnetic circuit 6 is disposed and provided with two energized windings 7 poled in opposition and disposed on the extreme rods of the magnetic circuit 6. A measuring winding 8 is disposed on the central rod of the magnetic circuit 6.

Two metal holders 9 secure the magnetic circuit 6 to cover 10 of the housing 1, the latter being provided with connecting pipes 11 and 12 for respectively supplying and draining a cooling agent, which is in this case water. A rubber sealing ring 13 is disposed between the housing 1 and the auxiliary housing 3.

The pickup is installed in a crystallizer 14 so that the bottom of the pickup housing 1 is part of the forming wall of the crystallizer and is in contact with interface 15 of two media 16 and 17, which is in this case fluid slag and molten metal. The housing 1 of the pickup is electrically insulated from the crystallizer 14 by means of an insulating gasket 18 made of a polyfluoroethylene resin.

Depending on the particular process conditions, with the ingots cast varying in cross section, the bottom of the pickup housing 1 should be so shaped as to correspond to part of the cross section of the ingot being cast over the area where the pickup is installed in the crystallizer 14.

One possible design of the proposed interface pickup is where the external and internal housings have spherically-shaped bottoms, the radius-vectors of curvature thereof being oriented in the same direction.

Figure 3:
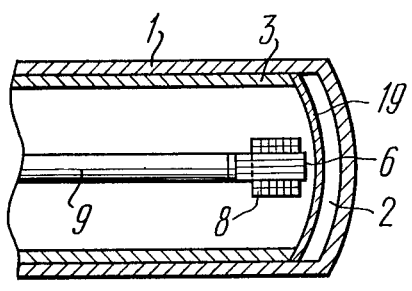
FIG. 3 illustrates the shape of the bottoms of the external and the auxiliary housings of the proposed pickup (longitudinal section)

In one such case, the bottom of the external housing 1 and bottom 19 (FIG. 3) of the auxiliary housing 3 are convex in shape.

Figure 4:
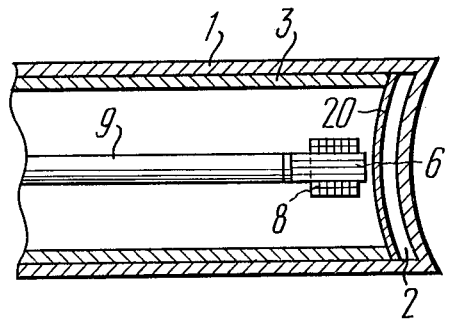
FIG. 4 illustrates an alternative shape of the bottoms of the external and the auxiliary housings of the proposed pickup (longitudinal section)

A third modification of the proposed interface pickup is possible when designed on similar lines as the one described hereinabove, but differing therefrom in that the bottom of the external housing 1 and bottom 20 (FIG. 4) of the auxiliary housing 3 are concave in shape.

A fourth modification of the proposed pickup is possible when built similarly to the embodiments described above.

Figure 6:
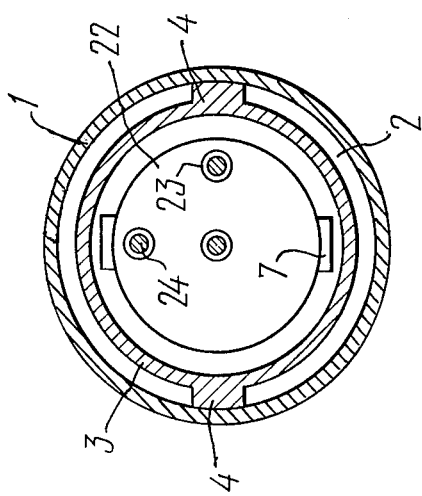
FIG. 6 is a diagrammatic view of a section taken along the line VI—VI of FIG. 5.
Figure 5:
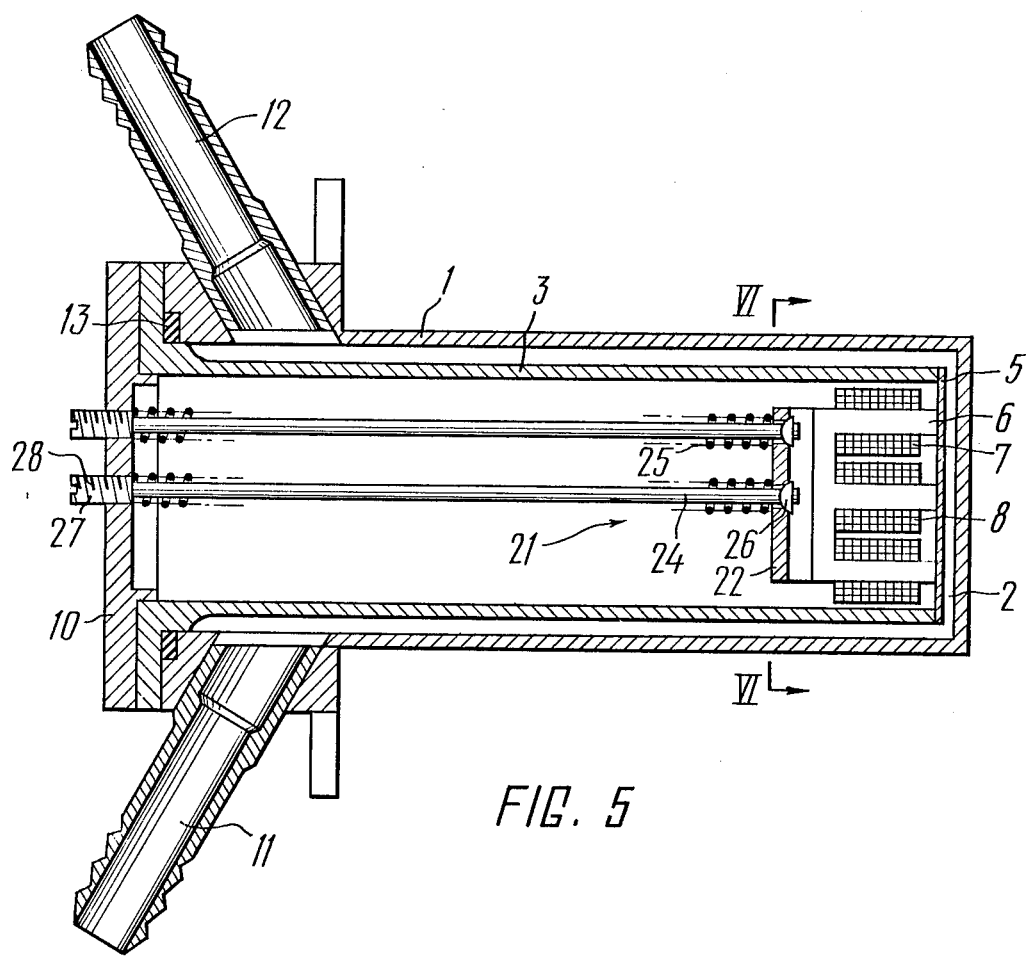
FIG. 5 is a longitudinal section of the proposed pickup with a mechanism for displacing the magnetic dircuit relative to the bottom of the auxiliary housing.

The latter embodiment is distinct from the others in that, in order to improve the accuracy of alignment of the pickup, the magnetic circuit 6 is provided with a mechanism 21 (FIG. 5) for displacing the magnetic circuit 6 relative to the bottom 5 of the auxiliary housing 3. The mechanism 21 comprises a plate 22 rigidly mounted on the magnetic circuit 6, the plate 22 being constructed from a non-magnetic material, which is in this case an austenitic steel having a resistivity of $50.10^{-6}$ ohm.cm. There are three apertures 23 formed in the plate 22 (FIG. 6), of which one is disposed on the longitudinal axis of the auxiliary housing 3 whereas the other two are arranged in two planes, one parallel and one perpendicular to the plane of the magnetic circuit 6 (FIG. 5), passing through each of these two apertures 23 (FIG. 6) and the aperture 23 disposed on the longitudinal axis of the auxiliary housing 3.

The mechanism 21 (FIG. 5) also comprises three rods 24, each mounting a spring 25 actuating the plate 22. One end 26 of the rods 24 is formed as a spherical bearing received into the respective aperture 23 (FIG. 6) of the plate 22. The other end 27 (FIG. 5) of each rod 24 is provided with a thread 28 whereby the end 27 is fitted into the cover 10.

Figure 7:
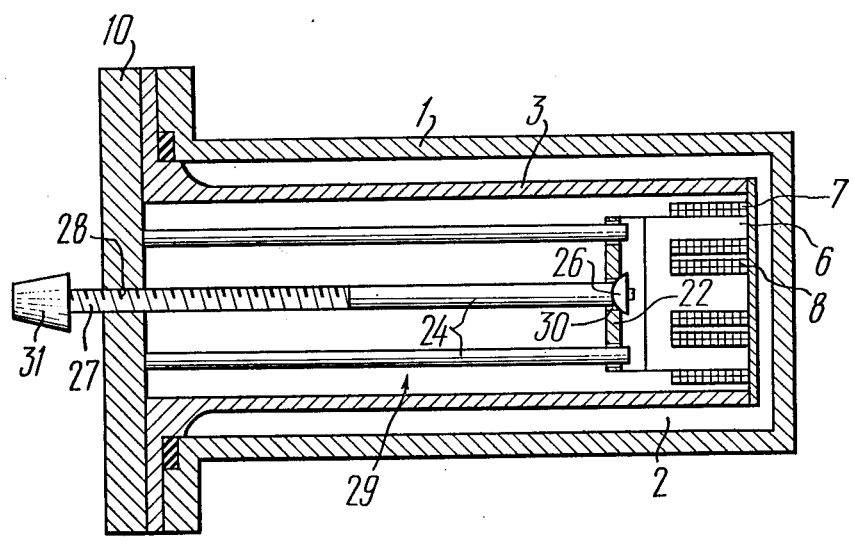
FIG. 7 is a longitudinal section of the proposed pickup with an alternative embodiment of a mechanism for displacing the magnetic circuit relative to the bottom of the auxiliary housing.

With such a design for the pickup, the magnetic circuit 6 being installed within the auxiliary housing 3 and insulated from the coolant, the pickup may employ an alternative mechanism 29 (FIG. 7) for displacing the magnetic circuit similar to the one described hereinabove.

The mechanism 29 is distinct from the mechanism 21 in that three apertures 30 formed in the plate 22 are so disposed that their axes lie in a single plane. The central aperture 30 receives the end 26 of the rod 24 formed as a spherical bearing, the other end 27 thereof being provided with a handle 31. The other two rods 24 are rigidly secured at one end in the cover 10, whereas their other ends are movably mounted in the respective apertures 30.

In the foregoing embodiments of the pickup, the magnetic circuit is installed within the auxiliary housing 3 so that the ends of the rods thereof are in contact with the bottom 5 of the housing 3. The thickness of the bottom 5 of the auxiliary housing 3 is 0.2 mm, and the material from which it is constructed is a titanium alloy having a resistivity of $100.10^{-6}$ ohms.cm.

The proposed pickup may be built according to a fifth design similar to the previously described embodiments thereof.

The fifth embodiment of the proposed pickup is distinguished by virtue of the fact that the thickness of the bottom 5, 19 or 20 of the auxiliary housing 3 is selected to be 0.05 mm, and the material from which this bottom is constructed is a titanium alloy having a resistivity of $50.10^{-6}$ ohms.cm.

Still another, sixth, embodiment of the proposed pickup is feasible which is similar to the ones described hereinabove.

It is distinguished by virtue of the fact that the thickness of the bottom 5, 19 or 20 of the auxiliary housing 3 is selected to be 0.35 mm, and the material from which this bottom is constructed is an austenitic steel having a resistivity of $120.10^{-6}$ ohms.cm.

The proposed interface pickup, whereof the embodiments have been described hereinabove, may likewise be employed for detecting a molten metal-metal interface.

The contactless inductance interface pickup of this invention operates in the following manner:

The pickup is rigidly mounted in the crystallizer 14 (FIG. 1) so that the bottom of the pickup housing 1 constitutes part of the forming surface of the crystallizer 14, with the cooling agent supplied from below and drained from above. The cooling agent supplied into the clearance 2 via the connecting pipe 11 and the lower passage, flows in the clearance between the bottom 5 of the auxiliary housing 3 and the bottom of the housing 1, cooling the latter.

In order to provide for a uniform cooling of the bottom of the housing 1 and, hence, to prolong the service life of the pickup, the clearance between the bottom of the housing 1 and the bottom 19 (FIG. 3) or 20 (FIG. 4) of the auxiliary housing 3 is made uniform which is achieved by selecting such a shape for the bottom 19 or 20 that duplicates the shape of the bottom of the housing 1.

The pickup is so positioned in the crystallizer 14 (FIG. 1) that the interface 15 of the media 16 and 17, the fluid slag and the molten metal, is aligned centrally with respect to the pickup, i.e. along the axis of the central rod of the magnetic circuit 6. The energized windings 7 of the magnetic circuit 6 are poled in opposition in order that the magnetic fields set up thereby may cancel out in the central rod of the magnetic circuit 6 which mounts the measuring winding 8.

In case the bottom of the external housing 1 is in contact only with the fluid slag 16, the magnetic fields set up by the energized windings 7 induce eddy currents in the slag 16 which equally reduce the intensity of these magnetic fields so that the output signal of the measuring winding 8 is equal to zero.

As the fluid slag - the molten metal interface 15 approaches the pickup center, the intensity of the magnetic field of one of the energized windings 7 closing through the molten metal 17 is reduced to a greater extent than that of the magnetic field set up by the other energized winding and closing through the fluid slag 16. This will cause the measuring winding 8 to produce an electric signal controlling the position of the crystallizer 14 with respect to the interface 15, maintaining it at a prescribed level in the course of electroslag remelting.

The proposed pickup is employed in electroslag, electron-beam and plasma-arc metallurgical processes as well as in electroslag welding, electroslag overlaying welding and continuous casting of metal with a view to determining the level of the molten metal relative to the forming surface of the crystallizer, thereby permitting unattended operation of the process.

It has already been mentioned that the pickup is so positioned in the crystallizer 14 that the plane passing through the ends of the rods of the magnetic circuit 6 is normal to the interface 15. In practice, this condition is sometimes difficult to meet, for example, in cases when the axis of the aperture in the crystallizer 14, whereinto the pickup is installed, is not normal to the forming surface of the crystallizer, causing an imbalance of the zero signal at the pickup output. A similar imbalance results if the bottom of the external housing 1 and the bottom 5, 19 (FIG. 3) or 20 (FIG. 4) of the auxiliary housing 3 (FIG. 5) are non-uniform in thickness or the energized windings 7 are differently wound or disposed.

In order to obviate these difficulties, the proposed pickup is provided with the mechanism 21 for displacing the magnetic circuit 6 relative to the bottom 5 of the auxiliary housing 6. By rotating the ends 27 of the rods 24, which is made possible thanks to the thread 28, the distance between the cover 10 of the housing 1 and the plate 22 rigidly linked with the magnetic circuit 6 is varied, by varying the distance between the rod ends of the magnetic circuit 6 and the bottom 5. By rotating the central rod 24 (FIG. 6) and one of the side rods 24, the magnetic circuit 6 (FIG. 5) is turned about the axis passing through these two rods 24, thereby eliminating the imbalance of the zero signal at the output of the pickup.

In another embodiment incorporating the mechanism 29 (FIG. 7), the magnetic circuit 6 is displaced in an axial direction, which is the only possible one as the side rods 24 merely serve as guides, the displacement being effected by use of the handle 31.

The proposed contactless inductance interface pickup embodied as described hereinabove offers some advantages over the prior art pickups, viz. the possibility of controlling and realigning the pickup during the course of operation without cutting off the coolant supply or dismantling the pickup, and a longer service life is achieved through positioning the magnetic circuit with the windings inside the auxiliary housing which insulates the magnetic circuit from the cooling agent, as well as through a uniform cooling of the pickup housing bottom.

What is claimed is:

1. A contactless inductance interface pickup for detecting the interface of two media differing in specific density and resistivity of which at least one is electrically conductive and non-magnetic, comprising: a first housing having a bottom and a cover; a second housing formed as a pot and having a bottom constructed from a non-magnetic material, the second housing being rigidly secured within the first housing to the cover of the first housing; a clearance defined by the first and second housings; means for supplying a cooling agent into the clearance; means for draining the cooling agent from the clearance; a magnetic circuit installed inside the second housing in immediate proximity to the bottom thereof and secured to the cover of the first housing; at least one measuring winding and at least one energized winding disposed on the magnetic circuit; the bottom of the second housing being of such a thickness as to allow the magnetic field of the pickup to reach the interface of the two media; and a mechanism for displacing the magnetic circuit relative to the bottom of the second housing, the mechanism being mechanically linked with the magnetic circuit and comprising: a non-magnetic plate rigidly secured on the magnetic circuit; three rods mechanically linked with the plate; a spring disposed on each of the rods and serving to actuate the plate; one end of each of the rods being movably mounted in the cover of the first housing; the other end of each of the rods being formed as a spherical bearing; apertures formed in the plate, the number of the apertures corresponding to the number of the rods, the apertures serving to accommodate the spherical bearings; one of the apertures disposed on the longitudinal axis of the second housing; the other two of the apertures so disposed as to lie in two planes, one parallel and one perpendicular to the plane of the magnetic circuit, and passing through each of the two apertures and the aperture disposed on the longitudinal axis of the second housing.

2. The pickup as set forth in claim 1, wherein the bottom of the first housing has a spherical shape and the bottom of the second housing likewise has a spherical shape, whose radius vector of curvature is oriented in the same direction as the radius vector of curvature of the bottom of the first housing.

3. The pickup as set forth in claim 1, wherein the thickness of the bottom of the second housing is within 0.05 to 0.35 mm.

4. The pickup as set forth in claim 3 wherein the non-magnetic material from which the bottom of the second housing is constructed is selected from the group consisting essentially of an austenitic steel and a titanium alloy each of which has a resistivity greater than $50.10^{-6}$ ohms. cm.

5. The pickup as set forth in claim 2, wherein the thickness of the bottom of the second housing is within 0.05 to 0.35 mm.

6. The pickup as set forth in claim 5, wherein the non-magnetic material from which the bottom of the second housing is constructed is selected from the group consisting essentially of an austenitic steel and a titanium alloy each of which has a resistivity greater than $50.10^{-6}$ ohms.cm.

7. A contactless inductance interface pickup for detecting the interface of two media differing in specific density and resistivity of which at least one is electrically conductive and non-magnetic, comprising: a first housing having a bottom and a cover; a second housing formed as a pot and having a bottom constructed from a nonmagnetic material, the second housing being rigidly secured within the first housing to the cover of the first housing; a clearance defined by the first and second housings; means for supplying a cooling agent into the clearance; means for draining the cooling agent from the clearance; a magnetic circuit installed within the second housing and secured to the cover of the first housing; poles of the magnetic circuit which are in contact with the bottom of the second housing; at least one measuring winding and at least one energized winding disposed on the magnetic circuit; the bottom of the second housing having a thickness thereof such as to allow the magnetic field of the pickup to reach the interface of the two media; and a mechanism for displacing the magnetic circuit relative to the bottom of the second housing, the mechanism being mechanically linked with the magnetic circuit and comprising: a non-magnetic plate rigidly secured on the magnetic circuit; three rods mechanically linked with the plate; a spring disposed on each of the rods and serving to actuate the plate; one end of each of the rods being movably mounted in the cover of the first housing; the other end of each of the rods being formed as a spherical bearing; apertures formed in the plate, the number of the apertures corresponding to the number of the rods, the apertures serving to accommodate the spherical bearings; one of the apertures disposed on the longitudinal axis of the second housing; the other two of the apertures so disposed as to lie in two planes, one parallel and one perpendicular to the plane of the magnetic circuit, and passing through each of the two apertures and the aperture disposed on the longitudinal axis of the second housing.

8. The pickup as set forth in claim 7, wherein the bottom of the first housing has a spherical shape and the bottom of the second housing likewise has a spherical shape, whose radius-vector of curvature is oriented in the same direction as the radius-vector of curvature of the bottom of the first housing.

9. The pickup as set forth in claim 7, wherein the thickness of the bottom of the second housing is within 0.05 to 0.35 mm.

10. The pickup as set forth in claim 9, wherein the non-magnetic material from which the bottom of the second housing is constructed is selected from the group consisting essentially of an austenitic steel and a titanium alloy each of which has a resistivity greater than $50.10^{-6}$ ohms.cm.

11. The pickup as set forth in claim 8, wherein the thickness of the bottom of the second housing is within 0.05 to 0.35 mm.

12. The pickup as set forth in claim 11, wherein the non-magnetic material from which the bottom of the second housing is constructed is selected from the group consisting essentially of an austenitic steel and a titanium alloy each of which has a resistivity greater than $50.10^{-6}$ ohms.cm.

* * * * *